United States Patent
Quattromani et al.

(10) Patent No.: US 11,903,864 B2
(45) Date of Patent: Feb. 20, 2024

(54) PEDIATRIC CHILD POSITION HOLDER AND METHODS OF USING SAME

(71) Applicant: Texas Tech University System, Lubbock, TX (US)

(72) Inventors: Frank Louis Quattromani, Lubbock, TX (US); Patricia Hull Rae Quattromani, Lubbock, TX (US)

(73) Assignee: TEXAS TECH UNIVERSITY SYSTEM, Lubbock, TX (US)

( * ) Notice: Subject to any disclaimer, the term of this patent is extended or adjusted under 35 U.S.C. 154(b) by 901 days.

(21) Appl. No.: 16/677,199

(22) Filed: Nov. 7, 2019

(65) Prior Publication Data

US 2020/0170828 A1 Jun. 4, 2020

Related U.S. Application Data

(60) Provisional application No. 62/773,347, filed on Nov. 30, 2018.

(51) Int. Cl.
| | |
|---|---|
| *A61F 5/37* | (2006.01) |
| *A61B 6/04* | (2006.01) |
| *A41D 13/12* | (2006.01) |

(52) U.S. Cl.
CPC ............ *A61F 5/37* (2013.01); *A41D 13/1272* (2013.01); *A61B 6/04* (2013.01); *A61F 5/3707* (2013.01); *A61B 2503/06* (2013.01)

(58) Field of Classification Search
CPC ........ A61F 5/37; A61F 5/3707; A61F 5/0193; A41D 13/1272; A41B 13/00; A41B 13/06; A41B 13/065; A47G 9/083; A61B 6/04; A61B 2503/06
See application file for complete search history.

(56) References Cited

U.S. PATENT DOCUMENTS

| | | | |
|---|---|---|---|
| 2,456,898 A | 12/1948 | Strandhagen | |
| 3,920,012 A | 11/1975 | Patel | |
| 3,933,154 A * | 1/1976 | Cabansag | ............. A61F 5/3776 378/208 |
| 4,142,522 A | 3/1979 | Hill | |
| 4,481,942 A | 11/1984 | Duncan | |
| 5,016,650 A | 5/1991 | Marlar | |
| 7,181,789 B2 | 2/2007 | Gatten | |
| 8,302,225 B1 | 11/2012 | Earnest | |
| 8,375,486 B2 | 2/2013 | Earnest | |

(Continued)

*Primary Examiner* — Keri J Nelson

(74) *Attorney, Agent, or Firm* — LOZA & LOZA, LLP; Kevin L. Soules

(57) ABSTRACT

A pediatric position holder for holding a child in a position is provided. The pediatric position holder includes a central panel extending longitudinally from a cranial portion to a caudal portion, arm flaps extending outwardly from opposing sides of the central panel, and leg flaps extending outwardly from opposing sides of the central panel. The arm flaps each include a proximal arm segment and a distal arm segment extending from the proximal arm segment. The leg flaps each include a proximal leg segment that defines one cutout and a distal leg segment extending from the proximal leg segment. The pediatric restraint is configurable between an initial, open configuration and a second, closed configuration in which the distal arm segments of the arm flaps overlap one another, and the distal leg segment of each of the leg flaps is positioned within the cutout of the respective leg flap.

17 Claims, 7 Drawing Sheets

(56) References Cited

U.S. PATENT DOCUMENTS

| | | |
|---|---|---|
| 8,505,542 B2 | 8/2013 | Boxall |
| 8,745,794 B1 * | 6/2014 | McDermott ........... A41B 13/06 5/655 |
| 8,955,181 B2 | 2/2015 | Kelly |
| 9,119,423 B2 | 9/2015 | Gotel et al. |
| 9,907,688 B2 * | 3/2018 | Pino .......................... A61F 7/08 |
| 2004/0149293 A1 | 8/2004 | Freedman |
| 2014/0150159 A1 | 6/2014 | Alluna |
| 2017/0055592 A1 * | 3/2017 | Stephan ................. A41B 13/06 |
| 2020/0037795 A1 * | 2/2020 | Bailey .................... A47G 9/068 |

\* cited by examiner

PEDIATRIC CHILD POSITION HOLDER AND METHODS OF USING SAME

CROSS-REFERENCE TO RELATED APPLICATIONS

This application claims priority to U.S. Provisional Patent Application Ser. No. 62/773,347, filed on Nov. 30, 2018, the disclosure of which is hereby incorporated by reference in its entirety.

BACKGROUND OF THE DISCLOSURE

The present disclosure relates generally to holding devices, and more specifically, to a holding device for holding children during medical imaging and/or medical procedures.

In the medical field, it is necessary to hold children during medical procedures for a variety of reasons. Holding children may make medical procedures faster and easier for healthcare providers administering and/or carrying out the procedures. For example, children, and especially infants, may need to be held or restrained for procedures that require the children to be still (e.g., for imaging purposes) and/or for procedures on arms or legs of the children (e.g., inserting an IV, taking blood, and/or administering vaccinations). The amount of needed restraint or holding of the children may vary from procedure to procedure. For example, when a child is imaged, it is common to hold or restrain the entire body of the child such that the images come out sharp. However, when a child needs blood drawn from an arm, it is typically only necessary to restrain or hold the other arm of the child such that the child is unable to interfere with the blood draw.

While devices that restrain children are known, the known devices include many deficiencies, especially for restraining or holding children for medical procedures. For example, known devices include zippers, VELCRO, buttons, buckles and other closure devices that may make the restraining device uncomfortable for the children and/or interfere with the imaging of the children (e.g., metal closure devices may show up on an image). Further, known devices generally are only able to completely restrain or hold the children (e.g., known devices do not allow only one arm of the child to be restrained or held or just the neck of the child to be restrained). When the child is completely restrained or held, the child may be uncomfortable (e.g., their torso—chest and abdomen—is unable to completely expand) and therefore may be more apt to want to move. Additionally, healthcare providers may have trouble checking circulation and vitals (e.g., by looking at hands and feet of the child) and may be unable to access portions of the child (e.g., the torso area). There are many other deficiencies of known devices.

Consequently, a restraining or holding device used to restrain or hold children is needed that has multiple functionalities, keeps children comfortable, and ensures that healthcare providers are able to quickly and efficiently restrain children such that they may carry out medical procedures on the children.

SUMMARY OF THE DISCLOSURE

In one aspect, a pediatric position holder for holding a child is provided. The pediatric position holder includes a central panel extending longitudinally from a cranial portion to a caudal portion, first and second arm flaps extending outwardly from opposing sides of the cranial portion of the central panel, and first and second leg flaps extending outwardly from opposing sides of the caudal portion of the central panel. The first and second arm flaps each include a proximal arm segment extending from the cranial portion of the central panel and a distal arm segment extending from the proximal arm segment. The first and second leg flaps each include a proximal leg segment extending from the caudal portion of the central panel that defines at least one cutout and a distal leg segment extending from the proximal leg segment. The pediatric position holder is configurable between an initial, open configuration and a second, closed configuration in which the distal arm segments of the first and second arm flaps overlap one another, and the distal leg segment of each of the first and second leg flaps is positioned within the at least one cutout of the respective first and second leg flap.

In another aspect, a method is provided. The method includes providing a pediatric position holder, and the pediatric position holder includes first and second arm flaps extending outwardly from opposing sides of the cranial portion of the central panel and first and second leg flaps extending outwardly from opposing sides of the caudal portion of the central panel. The first and second arm flaps each include a proximal arm segment extending from the cranial portion of the central panel and a distal arm segment extending from the proximal arm segment. The first and second leg flaps each include a proximal leg segment extending from the caudal portion of the central panel and a distal leg segment extending from the proximal leg segment and defining at least one cutout. The method further includes wrapping one of the first and second arm flaps over at least one arm of a child to hold the at least one arm of the child, wrapping one of the first and second leg flaps over one leg of the child, and inserting the distal leg segment of the one of the first and second leg flaps into the respective at least one cutout of the respective proximal leg segment to hold the one leg of the child.

These and other features, aspects and advantages of the present disclosure will become better understood with reference to the following description and appended claims. The accompanying drawings, which are incorporated in and constitute a part of this specification, illustrate embodiments of the disclosure and, together with the description, serve to explain the principles of the disclosure.

BRIEF DESCRIPTION OF THE DRAWINGS

Corresponding reference characters indicate corresponding parts throughout the several views of the drawings.

DETAILED DESCRIPTION OF THE DISCLOSURE

The present disclosure relates generally to restraining or holding devices, and more specifically to a restraining or position holding device for restraining or holding children during medical imaging and/or medical procedures.

Figure 1:
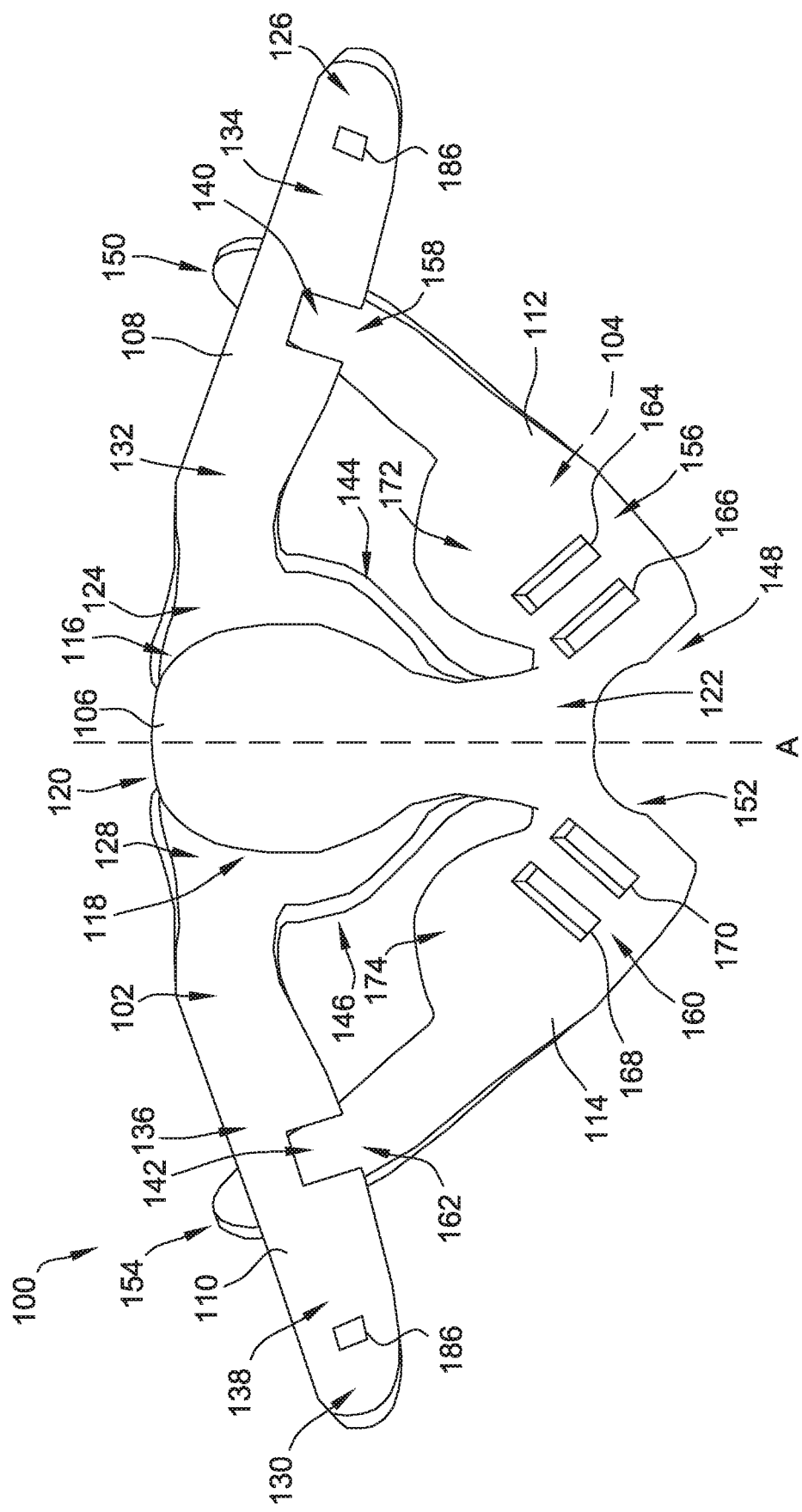
FIG. 1 is a front view of an exemplary pediatric restraint in an opened or unrestrained configuration.
Figure 2:
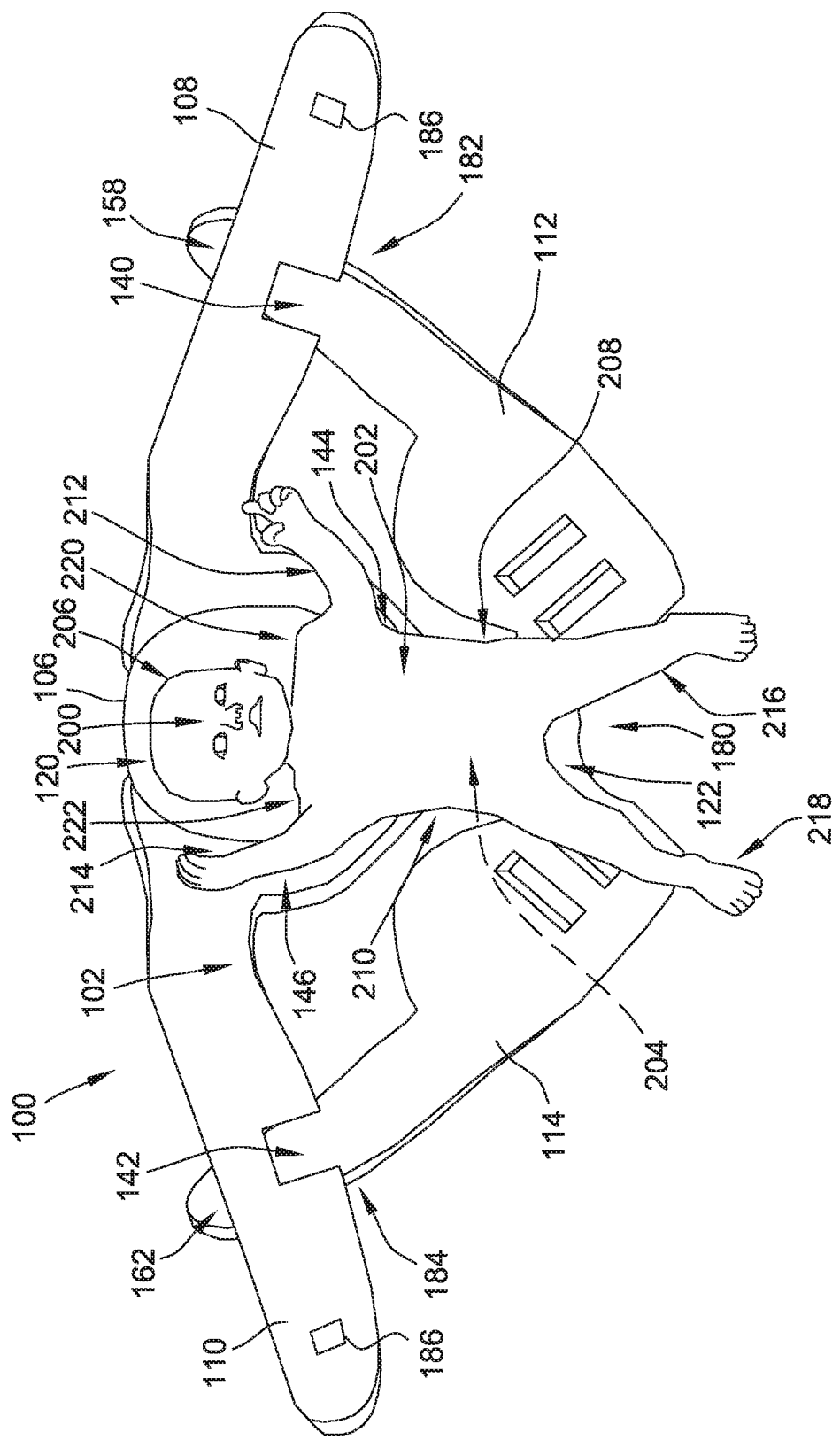
FIG. 2 is a front view of the pediatric restraint of FIG. 1 with a patient positioned therein.
Figure 3:
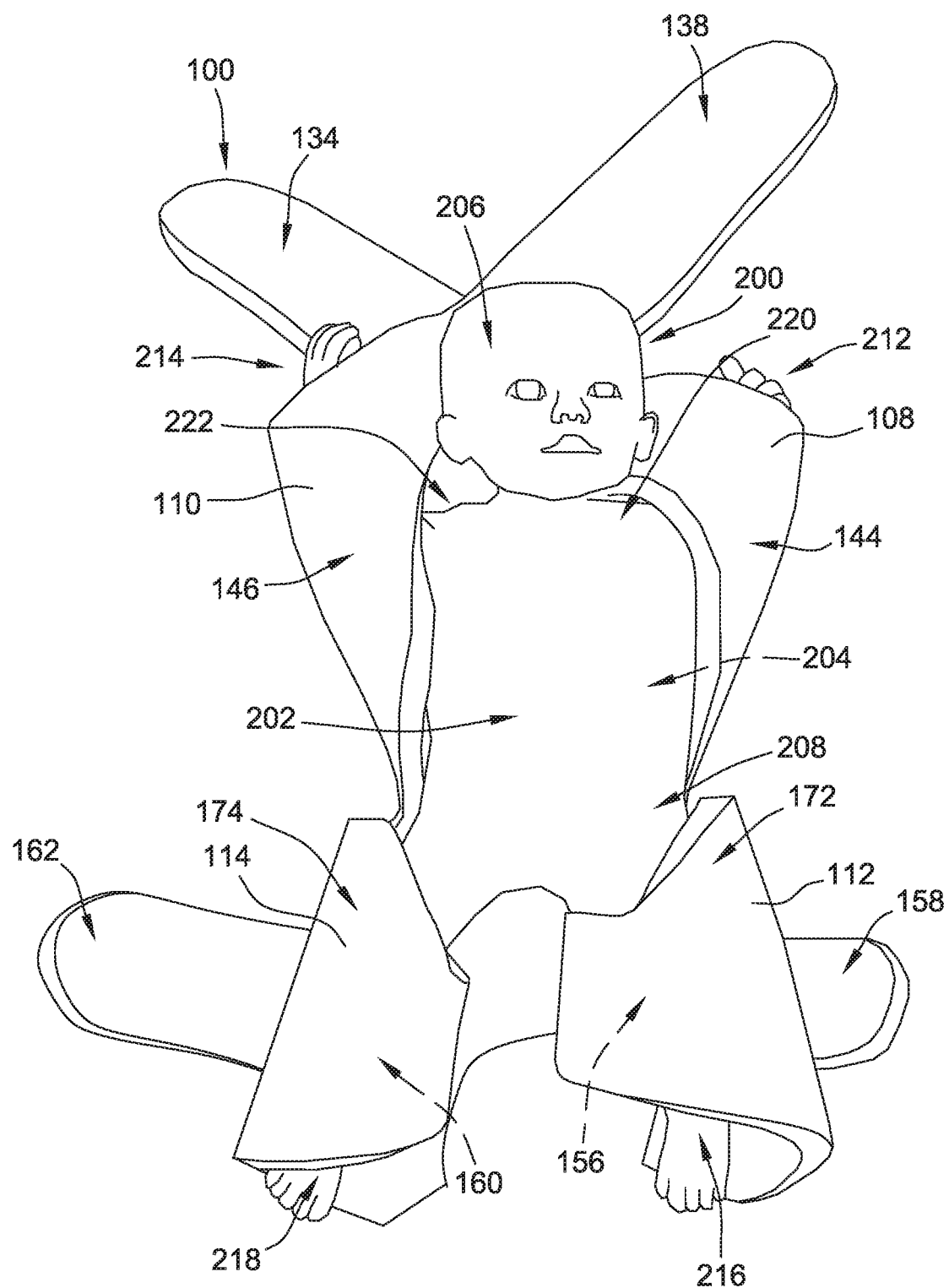
FIG. 3 is a front view of the pediatric restraint of FIG. 1 in a closed or restrained configuration that inhibits movement of patient.
Figure 4:
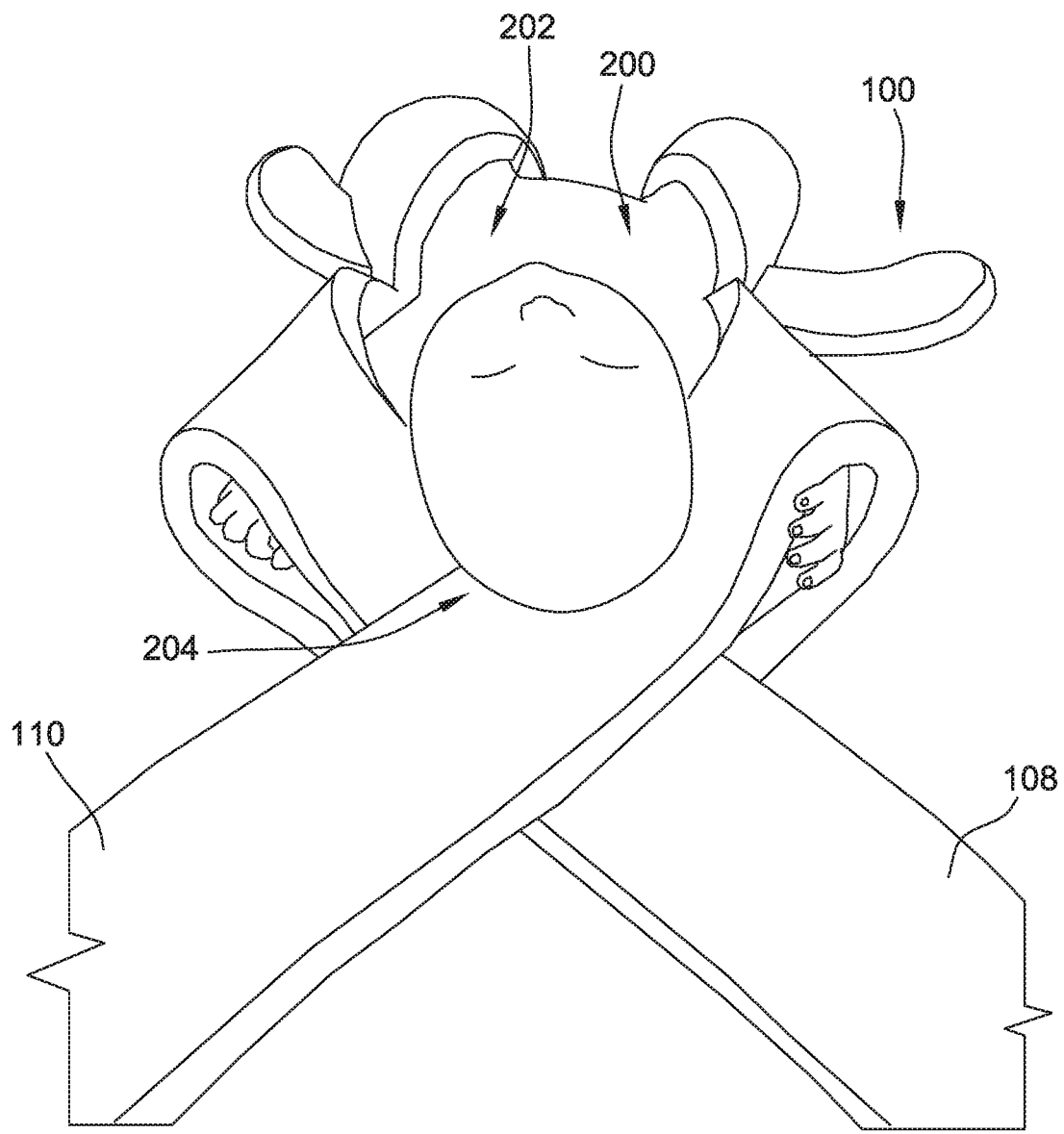
FIG. 4 is a top perspective view of the pediatric restraint in the closed or restrained configuration.
Figure 5:
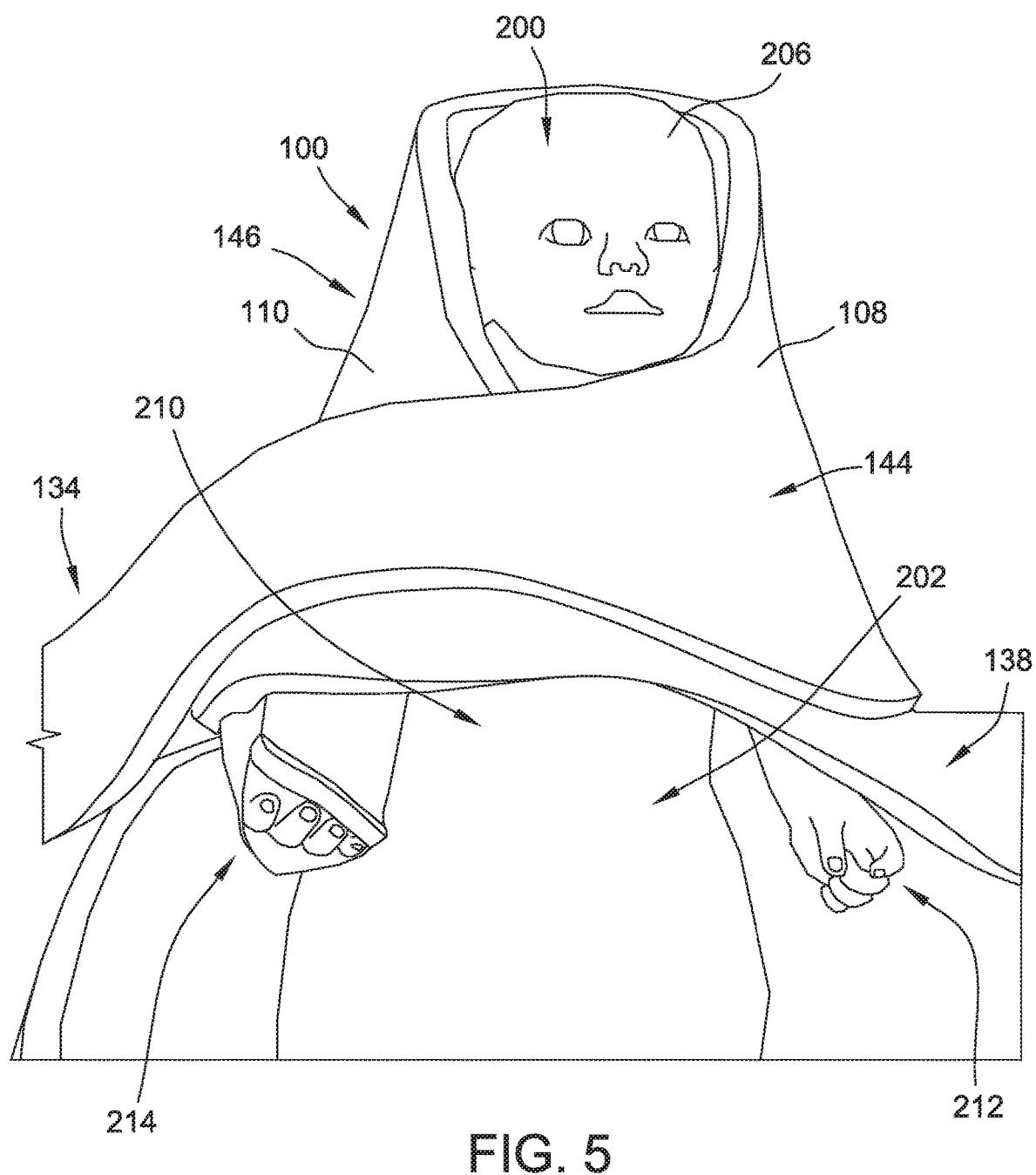
FIG. 5 is a front view of the pediatric restraint of FIG. 1 wrapped around the patient in a third closed or restrained configuration.

FIG. 1 is a front view of an exemplary position holder 100 in the form of a pediatric restraint 100 in an open or unrestrained configuration. FIG. 2 is a front view the pediatric restraint 100 of FIG. 1 with a patient 200 positioned therein, and FIGS. 3-5 are additional views of the pediatric restraint 100 in a different closed or restrained configurations in which movement of the patient 200 is inhibited. Although the pediatric restraint 100 is described and shown herein as being used with a child, specifically an infant, it should be understood that the pediatric restraint is not limited to use with children or infants, and may instead be used with any type of patient including, for example and without limitation, newborns, toddlers, adolescents, and adults.

In the exemplary embodiment, the pediatric restraint 100 is constructed from a flexible foam material. In other embodiments, the pediatric restraint 100 may be constructed from any other suitable material such that the pediatric restraint 100 may function as described herein. For example, in some embodiments, the pediatric restraint 100 may be constructed from a paper film and/or a plastic film such that the pediatric restraint 100 is disposable after use. Moreover, the pediatric restraint 100 may be constructed from several pieces of material that are coupled or secured together, or the pediatric restraint 100 may be formed from a single, unitary piece of material.

The pediatric restraint 100 has an interior surface 102 that generally faces the patient 200 when positioned within the restraint 100, and an exterior surface 104 that faces away from the patient 200. The pediatric restraint 100 includes a central panel 106, a first arm flap 108, a second arm flap 110, a first leg flap 112, and a second leg flap 114. The first and second arm flaps 108 and 110 are configured to restrain arms of the patient 200, and the first and second leg flaps 112 and 114 are configured to restrain legs of the patient 200, as shown and described in more detail with respect to FIGS. 3-5. The pediatric restraint 100 is generally symmetrical about a central vertical axis A. The central panel 106 extends horizontally from a first lateral edge 116 to a second lateral edge 118, and vertically from a cranial portion 120 to a caudal portion 122.

In the exemplary embodiment, the first and second arm flaps 108 and 110 extend outwardly from opposing edges 116, 118 of the cranial portion 120 of the central panel 106. Each of the first and second arm flaps 108 and 110 is elongate such that each of the first and second arm flaps 108 and 110 is configured to wrap around a portion of the patient 200, such as an arm of the patient 200 or shoulders of the patient 200, as described in more detail herein. The first arm flap 108 extends from a proximal end 124 to a distal end 126, and the second arm flap 110 extends from a proximal end 128 to a distal end 130. The proximal end 124 of the first arm flap 108 is generally aligned with the first lateral edge 116 of the central panel 106, and proximal end 128 of second arm flap 110 is generally aligned with the second lateral edge 118 of the central panel 106.

The first arm flap 108 includes a proximal segment 132 and a distal segment 134. The proximal segment 132 extends from the first lateral edge 116 to the distal segment 134, and the distal segment 134 extends from the proximal segment 132 to the distal end 126.

The second arm flap 110 includes a proximal segment 136 and a distal segment 138. The proximal segment 136 extends from the proximal end 128 to the distal segment 138, and the distal segment 138 extends from the proximal segment 136 to the distal end 130.

In the exemplary embodiment, the first arm flap 108 includes an arm flap cutout 140 between the proximal segment 132 and the distal segment 134, and the second arm flap 110 includes an arm flap cutout 142 between the proximal segment 136 and the distal segment 138. The arm flap cutout 140 of the first arm flap 108 is sized and shaped to receive a distal segment 158 of the first leg flap 112, and the arm flap cutout 142 of the second arm flap 110 is sized and shaped to receive a distal segment 162 of the second leg flap 114, as described in more detail herein. In the illustrated embodiment, the arm flap cutouts 140 and 142 are rectangular shaped. In other embodiments, the arm flap cutouts 140 and 142 may have any suitable shape such that the arm flap cutouts may receive the respective distal segments 158 and 162 of the respective first and second leg flaps 112 and 114 therein. In further embodiments, the first and second arm flaps 108 and 110 do not include the cutouts 140 and 142.

Further, in the exemplary embodiment, the distal segments 134 and 138 of first and second arm flaps 108 and 110, respectively, include attachment holes 186. Attachment holes 186 may be configured to receive an attachment (e.g., a hook or VELCRO) to secure the restraint device 100 in the second, restrained position, as shown in FIG. 3. In the exemplary embodiment, only the arm flaps 108 and 110 are illustrated as having attachment holes 186, though it should be understood that the leg flaps 112 and 114 may also include one or more attachment holes. Further the arm flaps 108 and 110 and/or the leg flaps 112 and 114 may each include more than one attachment hole 186.

In the exemplary embodiment, first arm flap 108 includes a first shoulder portion 144 at the proximal end 124 that extends vertically (i.e., parallel to axis A) along the first lateral edge 116 of the central panel 106. The second arm flap 110 similarly includes a second shoulder portion 146 at the proximal end 128 that extends vertically along the second lateral edge 118 of the central panel 106. The first and second shoulder portions 144 and 146 have an arcuate shape complementary to the respective first and second lateral edges 116 and 118. First and second shoulder portions 144 and 146 are configured to engage and restrain or inhibit movement of shoulders of the patient 200, as described below in more detail. In other embodiments, first and second shoulder portions 144 and 146 may have any suitable shape such that enables the first and second shoulder portions 144 and 146 function as described herein.

In the exemplary embodiment, the first and second leg flaps 112 and 114 extend outwardly from opposing edges of the central panel 106. The first and second leg flaps 112 and 114 elongate such that each of the first and second leg flaps 112 and 114 is configured to wrap around at least one leg of the child in the second, restrained configuration. The first leg flap 112 extends from a proximal end 148 to a distal end 150, and the second leg flap 114 extends from a proximal end 152 to a distal end 154. The first leg flap 112 includes a proximal segment 156 and a distal segment 158. The proximal segment 156 extends from the proximal end 148 to the distal segment 158, and the distal segment 158 extends from the proximal segment 156 to the distal end 150. The second leg flap 114 includes a proximal segment 160 and a distal segment 162. The proximal segment 160 extends from the proximal end 152 to the distal segment 162, and the distal segment 162 extends from the proximal segment 160 to the distal end 154.

In the exemplary embodiment, the proximal segment 156 of the first leg flap 112 includes a first cutout 164 and a second cutout 166, and the proximal segment 160 of the second leg flap 114 includes a first cutout 168 and a second cutout 170. The cutouts 164, 166, 168, and 170 of the respective first and second leg flaps 112 and 114 are configured to receive the respective distal segments 158 and 162 of the respective first and second leg flaps 112 and 114. Accordingly, the cutouts 164, 166, 168, and 170 have a shape and size that correspond with the shape and size of the distal segments 158 and 162.

Each distal segment 158 and 162 of the first and second leg flaps 112 and 114 is selectively insertable into one of the first and second cutouts 164, 166, 168, and 170 of the corresponding proximal segment 156 and 160 to selectively vary a size of an opening defined by each of the first and second leg flaps 112 and 114 when the pediatric restraint 100 is in the second, restrained configuration, as shown in FIG. 3. The leg flaps 112 and 114 are thereby configured to accommodate patients with different sized legs, and/or to allow the tightness of the restraint 100 around the patient's legs to be selectively varied.

In the exemplary embodiment, the cutouts 164, 166, 168, and 170 have the same size and shape. In other embodiments, the cutouts 164, 166, 168, and 170 may have different shapes and sizes. In the exemplary embodiment, each leg flap 112 and 114 includes two cutouts. In other embodiments, each of the first and second leg flaps 112 and 114 may include more or fewer cutouts than two cutouts, such as one cutout, three cutouts, four cutouts, or more cutouts. In yet other embodiments, the first and second leg flaps 112 and 114 may not include any cutouts.

In the exemplary embodiment, the proximal segment 156 of the first leg flap 112 includes a hip portion 172, and the proximal segment 160 of the second leg flap 114 includes a hip portion 174. The hip portions 172 and 174 extend along the proximal segments 156 and 160 of the respective first and second leg flaps 112 and 114. The hip portions 172 and 174 have an arcuate shape and are configured to engage hips 208 of the patient 200 and to restrain or inhibit movement of the hips 208 of the patient 200, as described in more detail herein. Further, in the exemplary embodiment, the proximal end 148 of the first leg flap 112 includes an arcuate edge 176, and the proximal end 152 of the second leg flap 114 also includes an arcuate edge 178. The arcuate edges 176 and 178 define an arcuate gap or cutout 180 between the first and second leg flaps 112 and 114. The arcuate gap 180 allows the first and second leg flaps 112 and 114 to move independently from one another (i.e., if the first leg flap 112 is raised, the second leg flap 114 may stay relatively flat).

Referring to FIG. 2, during use, the patient 200 is placed in the pediatric restraint 100 while the pediatric restraint 100 is in an opened or unrestrained configuration (shown in FIG. 2). Specifically, in one embodiment, a posterior part 204 of the patient 200 is positioned in engagement with the interior surface 102 of the pediatric restraint 100. The patient 200 is placed in the pediatric restraint 100 such that a head 206 of the patient 200 is aligned with and engages the cranial portion 120 of the central panel 106, and the hips 208 of the patient 200 are aligned with and engage the caudal portion 122 of the central panel 106. Further, a torso 210 of the patient 200 engages the central panel 106, a first shoulder 220 of the patient 200 engages the first shoulder portion 144 of the first arm flap 108, and a second shoulder 222 of the patient 200 engages the second shoulder portion 146 of the second arm flap 110. The arcuate gap 180 between the first and second leg flaps 112 and 114 is shaped complementary to the open space or gap between the patient's legs 216 and 218. As described in more detail herein, the first and second arm flaps 108 and 110 are used to restrain or inhibit movement of a first arm 212 and a second arm 214 of the patient 200, and the first and second leg flaps 112 and 114 are used to restrain or inhibit movement of a first leg 216 and a second leg 218 of the patient 200.

As shown in FIG. 2, when the pediatric restraint 100 is in the opened or unrestrained position, the arm flap cutouts 140 and 142 of first and second arm flaps 108 and 110 are aligned with the distal segments 158 and 162 of the first and second leg flaps 112 and 114, respectively. In some embodiments, an edge 182 of the distal segment 158 of the first leg flap 112 is received in the arm flap cutout 140 of the first arm flap 108, and an edge 184 of the distal segment 162 of the second leg flap 114 is received in the arm flap cutout 142 of the second arm flap 110. In such embodiments, the distal segments 158 and 162 are held in place by the arm flap cutouts 140 and 142 to maintain the pediatric restraint in the opened configuration to facilitate placing the patient 200 in the pediatric restraint 100. For example, in some embodiments, the first and second arm flaps 108 and 110 and/or the first and second leg flaps 112 and 114 may have a natural tendency to wrap or fold across the central panel 106 in the absence of an applied force, which might otherwise interfere with positioning the patient 200 within the pediatric restraint. Positioning the distal segments 158 and 162 of the first and second leg flaps 112 and 114 within the arm flap cutouts 140 and 142, respectively, holds the arm flaps 108 and 110 and the leg flaps 112 and 114 in place. Additionally, maintaining the arm flaps 108 and 110 and the leg flaps 112 and 114 in a secured position away from the central panel 106 reduces the likelihood of the patient 200 grabbing or contacting the arm flaps 108 and 112 and/or the leg flaps 112 and 114 while the patient 200 is being positioned in the restraint 100, which might otherwise cause the pediatric restraint 100 to move.

FIG. 3 illustrates the pediatric restraint 100 in a closed or restrained position in which the patient 200 is restricted or inhibited from moving. FIG. 4 is a top perspective view of the patient 200 and the pediatric restraint in the closed or restrained position. In this configuration, the arms 212 and 214 of the patient 200 are restrained from moving by the first and second arm flaps 108 and 110, and the legs 216 and 218 of the patient 200 are restrained from moving by the first and second leg flaps 112 and 114. The elongate shape of the arm flaps 108 and 110 allows the arm flaps 108 and 110 to be wrapped around and restrain the arms 212 and 214 of the patient 200. Similarly, the elongate shape of the leg flaps 112 and 114 allows the leg flaps 112 and 114 to be wrapped around and restrain the legs 216 and 218 of the patient 200.

In the embodiment illustrated in FIGS. 3 and 4, the arms 212 and 214 of the patient 200 are restrained by the first and second arm flaps 108 and 110 by overlapping the arm flaps 108 and 110 behind the posterior part 204 of the patient's head 206, as illustrated in FIG. 4. More specifically, the distal segments 134 and 138 of the respective first and second arm flaps 108 and 110 are wrapped around the respective arms 212 and 214 of the patient 200, and overlapped behind the patient's head 206 such that the distal segment 138 of the second arm flap 110 is placed in overlapping relationship with the distal segment 134 of the first arm flap 108. When the distal segments 134 and 138 of the respective first and second arm flaps 108 and 110 are overlapped, the first shoulder portion 144 of the first arm flap 108 engages the first shoulder 220 of the patient 200, and the second shoulder portion 146 of the second arm flap 110 engages the second shoulder 222 of the patient 200. The weight of the head 206 of the patient 200 keeps the first and second arm flaps 108 and 110 in the overlapped configuration and therefore keeps the arms 212 and 214 of the patient 200 restrained.

Additionally, in the embodiment illustrated in FIG. 3, the first leg 216 of the patient 200 is restrained by the first leg flap 112, and the second leg 218 of the patient 200 is restrained by the second leg flap 114. More specifically, the distal segment 158 of the first leg flap 112 is wrapped around the patient's first leg 216 and inserted through one of the first cutout 164 and the second cutout 166 of the proximal segment 156 of the first leg flap 112. The distal segment 162 of the second leg flap 114 is wrapped around the patient's second leg 218 and inserted through one of the first cutout 168 and the second cutout 170 of the proximal segment 160 of the second leg flap 114. That is, the respective distal segments 158 and 162 of the respective first and second leg flaps 112 and 114 are wrapped around the legs 216 and 218 of the patient 200 and inserted in the respective first or second cutouts 164, 166, 168, or 170 of the respective proximal segments 156 and 160 of the respective first and second leg flaps 112 and 114. The user of the pediatric restraint 100 (e.g., a healthcare professional) may select which of the first and second cutouts 164, 166, 168, or 170 to insert the distal segments 158 and 162 of the respective leg flaps 112 and 114 through based on the size of the patient's legs 216 and 218 and the desired tightness of the pediatric restraint 100 on the patient 200.

When the distal segments 158 and 162 are wrapped around the legs 216 and 218 of the patient, the respective hip portions 172 and 174 of the first and second leg flaps 112 and 114 engage with the hips 208 of the patient. The weight of the legs 216 and 218 of the patient and friction between the first and second cutouts 164, 166, 168, and 170 and the distal ends 158 and 162 keep the first and second leg flaps 112 and 114 in the restrained position and therefore keep the legs 216 and 218 of the patient 200 restrained.

In FIG. 3, the patient 200 is shown with both arms 212 and 214 and both legs 216 and 218 restrained. In other embodiments, the arms 212 and 214 and legs 216 and 218 of the patient 200 can be restrained in any suitable manner that enables the pediatric restraint 100 to function as described herein. In some embodiments, for example, one or more the patient's arms 212 and 214 and/or legs 216 and 218 may be left unrestrained so that a healthcare professional may have easier access to the patient 200. For example, if the patient 200 requires an IV in second arm 214, only the first arm 212 and the legs 216 and 218 may be restrained so that a healthcare professional can access the arm 214 of the patient 200.

Referring to FIG. 5, the patient 200 is shown restrained by the pediatric restraint 100 in another restrained configuration. In this configuration, the arms 212 and 214 of the patient 200 are restrained by the first and second arm flaps 108 and 110 in a different configuration than that shown in FIGS. 3 and 4. Specifically, the first and second arm flaps 108 and 110 are wrapped around the anterior part 202 of the patient 200 such that the first and second arm flaps 108 and 110 contact the anterior part 202 of the torso 210 of the patient 200 to restrain the arms 212 and 214. In this configuration, the first and second arm flaps 108 and 110 may be wrapped around and tucked under the back or posterior part 204 of the patient 200 to secure the first and second arm flaps 108 and 110 in the restrained configuration.

Each of the first and second arm flaps 108 and 110 may restrain one or both of the arms 212 and 214 of the patient 200. In some embodiments, for example, each of the first and second arm flaps 108 and 110 secures a single arm of the patient 200 by wrapping around only one respective arm 212 or 214 (as shown in FIGS. 3 and 4). In other embodiments, each of the first and second arm flaps 108 and 110 may restrain both arms 212 and 214 of the patient 200 by wrapping over both arms 212 and 214 (as shown in FIG. 5).

Figure 6:
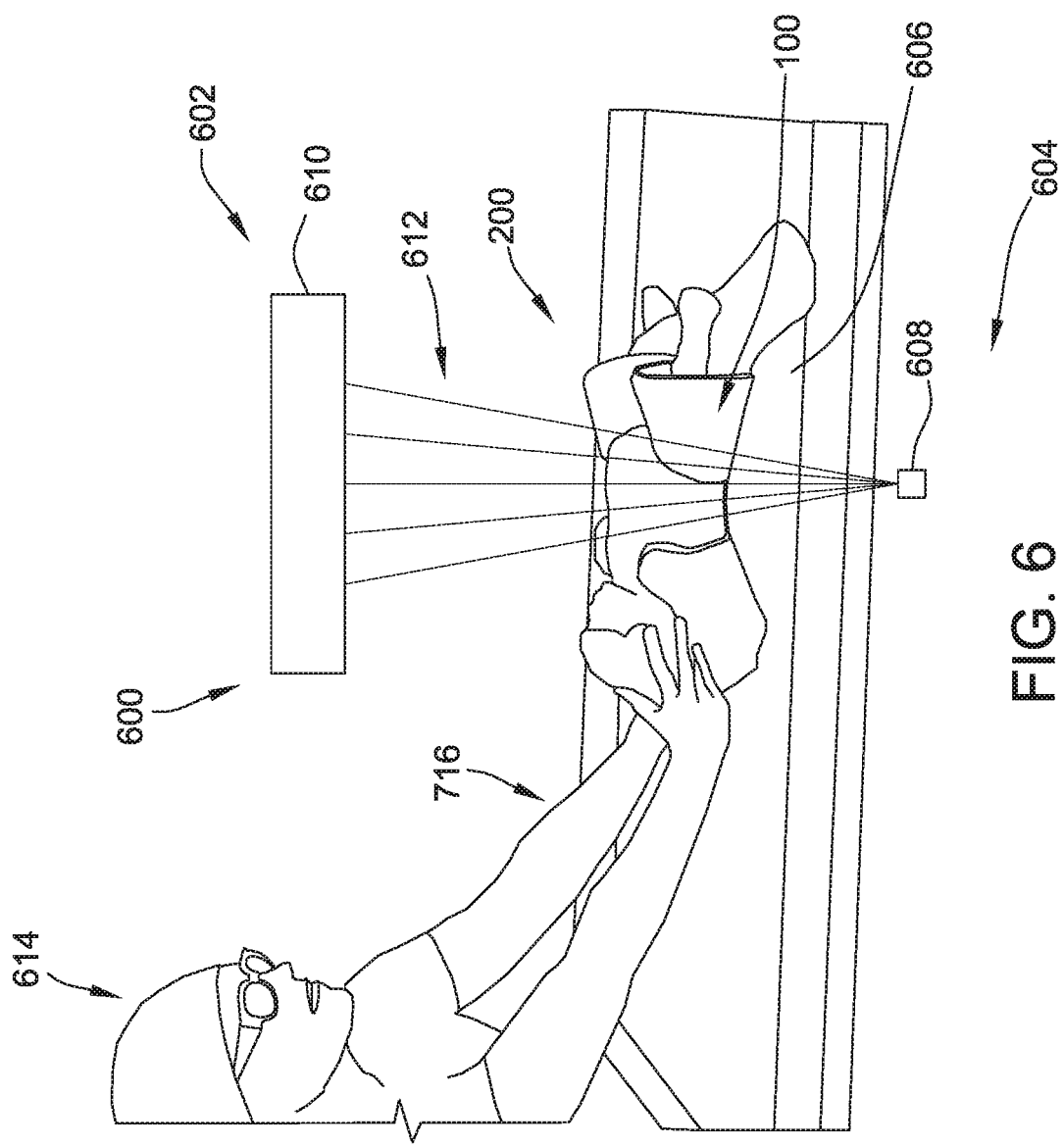
FIG. 6 is a side view of the pediatric restraint of FIG. 1 being used in a medical imaging procedure.

FIG. 6 illustrates the pediatric restraint 100 being used in a medical procedure that includes a medical imaging device 600. In the exemplary embodiment, the medical imaging device 600 scans from a bottom portion 604 (e.g., near a floor of the medical imaging room) to a top portion 602 (e.g., near a ceiling of a medical imaging room). The medical imaging device 600 includes a table 606, an X-ray source 608, and an X-ray receiver 610. The patient 200 is supported by the table 606, and the table 606 is coupled to the X-ray source 608 (e.g., near the bottom portion 604). The X-ray source 608 generates X-rays 612 that radiate upward through the patient 200 to the X-ray receiver 610 (e.g., the X-rays 612 radiate from the bottom portion 604 upward to the top portion 602 of the medical imaging device 600).

In the illustrated embodiment, the medical imaging device 600 is an X-ray imaging device. In other embodiments, the medical imaging device 600 may be any other suitable imaging device that enables medical imaging of the patient 200 including, for example and without limitation, ultrasound imaging, magnetic resonance imaging (MRI), computed tomography (CT), and positron emission tomography (PET).

In known medical imaging devices (e.g., the medical imaging device 600), it is desirable that the patient 200 remain still for the imaging process to facilitate obtaining sharp images of the patient. Accordingly, the pediatric restraint 100 restrains the patient 200 such that the patient 200 may be imaged quickly and clearly by the medical imaging device 600. Further, in restraining the patient 200, the pediatric restraint 100 may ensure that the patient 200 does not require additional imaging, which may protect the patient 200 from unnecessary radiation (e.g., from additional scans).

In some embodiments, the patient 200 may need to be further restrained (e.g., by an operator 614) in the medical imaging device 600. For example, the operator 614 may stabilize the head and/or neck of the patient 200. Since the pediatric restraint 100 fully restrains the arms and legs of the patient 200, the operator 614 only needs minimal, if any, contact with the patient 200 to fully stabilize and restrain the patient 200 for imaging. Accordingly, the infant protection device 100 ensures that the operator 614 is not exposed to unnecessary radiation. In the illustrated embodiment, for example, the operator 614 only contacts the head of the patient 200, and therefore, the X-rays 612 do not directly contact the operator 614, and the operator 614 has minimal exposure to radiation.

Figure 7:
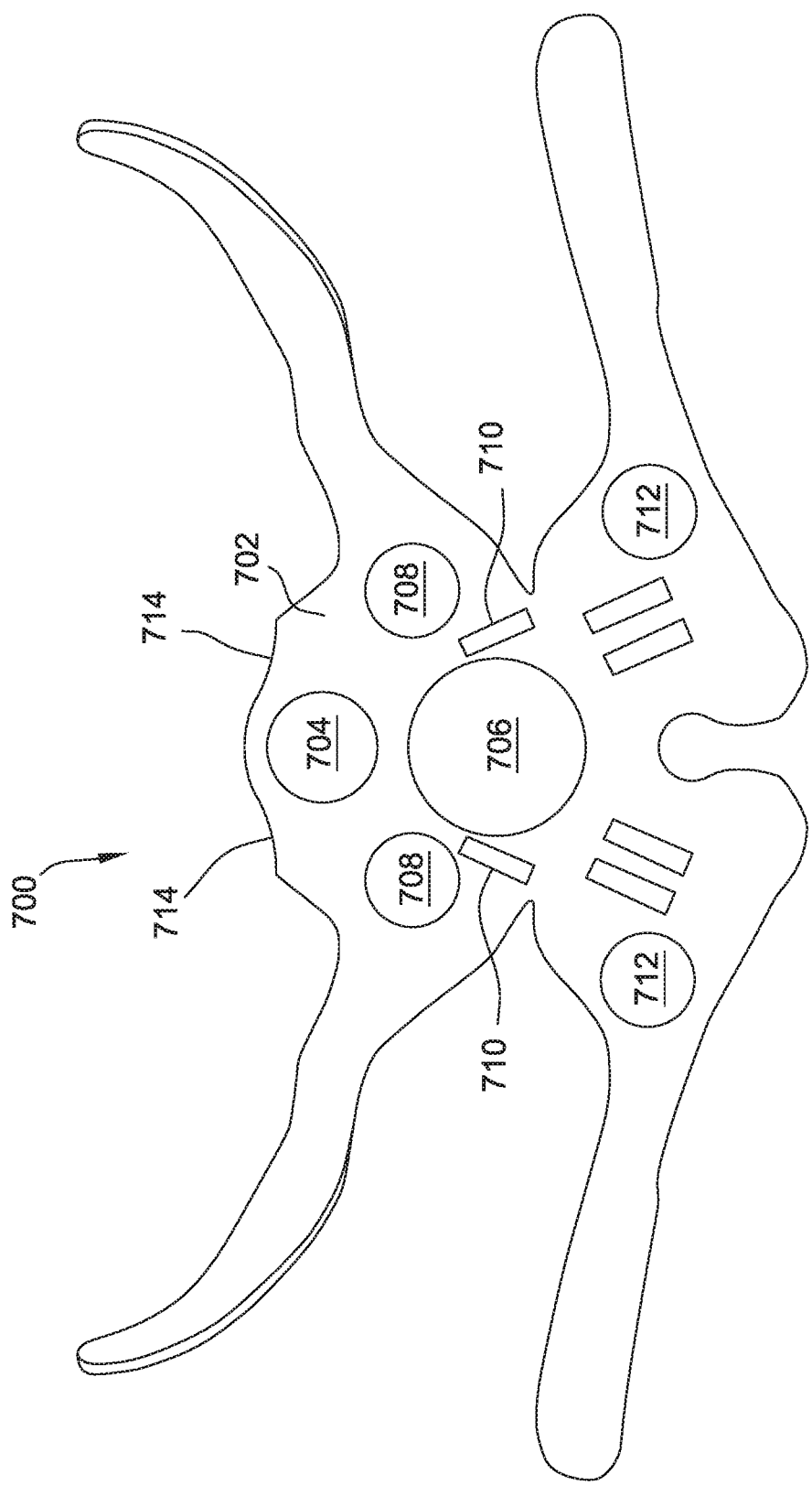
FIG. 7 is a front view of another embodiment of a pediatric restraint.

FIG. 7 shows another embodiment of an infant position holder in the form of a pediatric restraint 700. The pediatric restraint 700 is similar to the pediatric restraint 100, and includes substantially the same components as the pediatric restraint 100 (e.g., first and second arm flaps 108 and 110 and first and second leg flaps 112 and 114), and restrains a patient (e.g., patient 200, shown in FIGS. 2-5) in substantially the same way. The pediatric restraint 700 includes a central portion 702, and the central portion 702 may include a first cutout 704 and a second cutout 706. The first cutout 704 may be used to image and/or access the head/neck of the patient, and the second cutout 706 may be used to image and/or access the abdomen/back of the patient.

Further, the first and second arm flaps may include elbow cutouts 708 (e.g., in a proximal portion of the arm flaps adjacent to the central portion 702). The elbow cutouts 708 may be used to image and/or access elbows and/or portions of the arms of the patient. The central portion 702 may include arm flap cutouts 710. The arm flap cutouts 710 may be configured (e.g., sized and shaped) to receive a portion of the arm flaps therein. The leg flaps may include knee cutouts 712, used to image and/or access knees and/or portions of the legs of the patient. The central portion 702 may also include ear cutouts 714 used to image and/or access ears and/or portions of the head of the patient.

Although the embodiments and examples disclosed herein have been described with reference to particular embodiments, it is to be understood that these embodiments and examples are merely illustrative of the principles and applications of the present disclosure. It is therefore to be understood that numerous modifications can be made to the illustrative embodiments and examples and that other arrangements can be devised without departing from the spirit and scope of the present disclosure as defined by the claims. Thus, it is intended that the present application cover the modifications and variations of these embodiments and their equivalents.

This written description uses examples to disclose the disclosure, including the best mode, and also to enable any person skilled in the art to practice the disclosure, including making and using any devices or systems and performing any incorporated methods. The patentable scope of the disclosure is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

What is claimed is:

1. A pediatric position holder for holding a child, the pediatric position holder comprising:
    a central panel extending longitudinally from a cranial portion to a caudal portion;
    first and second arm flaps extending outwardly from opposing sides of the cranial portion of the central panel, wherein each of the first and second arm flaps comprises:
        a proximal arm segment extending from the cranial portion of the central panel; and
        a distal arm segment extending from the proximal arm segment; and
    first and second leg flaps extending outwardly from opposing sides of the caudal portion of the central panel, wherein each of the first and second leg flaps comprises:
        a proximal leg segment extending from the caudal portion of the central panel and defining at least one cutout; and
        a distal leg segment extending from the proximal leg segment,
    wherein the pediatric position holder is configurable between an initial, open configuration and a second, closed configuration in which the distal arm segments of the first and second arm flaps overlap one another, and the distal leg segment of each of the first and second leg flaps is positioned within the at least one cutout of the respective first and second leg flap, and wherein the caudal portion of the central panel comprises an arcuate cutout, wherein the arcuate cutout allows the first and second leg flaps to move independently of one another.

2. The pediatric position holder of claim 1, wherein the cranial portion has a rounded shape to complement a head of the child, and wherein the caudal portion has an arcuate shape to complement hips of the child.

3. The pediatric position holder of claim 1, wherein each of the first and second arm flaps is elongate such that each of the first and second arm flaps is configured to wrap around at least one of an arm of the child and shoulders of the child in the second, closed configuration, and wherein each of the first and second leg flaps is elongate such that each of the first and second leg flaps is configured to wrap around at least one leg of the child in the second, closed configuration.

4. The pediatric position holder of claim 1, wherein each distal arm segment of the first and second arm flaps is constructed from a flexible material such each distal arm segment is configured to wrap around at least one of an arm of the child and shoulders of the child in the second, closed configuration.

5. The pediatric position holder of claim 1, wherein each distal leg segment of the first and second leg flaps is constructed from a flexible material such that each distal leg segment of the first and second leg flaps is configured to be inserted through the at least one cutouts of the proximal leg segments in the second, closed configuration.

6. The pediatric position holder of claim 5, wherein the at least one cutout of each proximal leg segment of the first and second leg flaps comprises a first and a second cutout, and wherein each distal leg segment of the first and second leg flaps is selectively insertable into one of the first and second cutouts of the corresponding proximal leg segment to selectively vary a size of an opening defined by each of the first and second leg flaps when in the second, closed configuration.

7. The pediatric position holder of claim 1, wherein the central panel comprises at least one cutout that is shaped to allow access to a posterior part of the child when the pediatric position holder is in the second, closed configuration.

8. The pediatric position holder of claim 1, wherein the distal arm segments of the first and second arm flaps comprise an attachment hole, wherein the attachment hole is shaped to receive an attachment, and wherein the attachment is configured to secure the pediatric position holder in the second, closed configuration.

9. The pediatric position holder of claim 1, wherein the central panel comprises at least one cutout that is shaped to receive the distal arm segment of at least one of the first and second arm flaps when the pediatric position holder is in the second, closed configuration.

10. The pediatric position holder of claim 1, wherein the pediatric position holder is constructed from at least one of foam, plastic, paper, and combinations thereof.

11. A method comprising:
    providing a pediatric position holder, the pediatric position holder including:
        a central panel extending longitudinally from a cranial portion to a caudal portion;

first and second arm flaps extending outwardly from opposing sides of the cranial portion of the central panel, wherein each of the first and second arm flaps comprises:
   a proximal arm segment extending from the cranial portion of the central panel; and
   a distal arm segment extending from the proximal arm segment; and
first and second leg flaps extending outwardly from opposing sides of the caudal portion of the central panel, wherein each of the first and second leg flaps comprises:
   a proximal leg segment extending from the caudal portion of the central panel; and
   a distal leg segment extending from the proximal leg segment, the proximal leg segment defining at least one cutout,
wrapping one of the first and second arm flaps over at least one arm of a child to restrain the at least one arm of the child;
overlapping the first and second arm flaps behind a head of the child; and
securing the overlapped first and second arm flaps behind the cranial portion of the central panel,
wrapping one of the first and second leg flaps over one leg of the child; and
inserting the distal leg segment of the one of the first and second leg flaps into the respective at least one cutout of the respective proximal leg segment to hold the one leg of the child.

12. The method of claim 11, further comprising:
placing the child in the pediatric position holder such that a head of the child is placed in the cranial portion and hips of the child are placed in the caudal portion.

13. The method of claim 11, further comprising overlapping the first and second arm flaps over an anterior portion of a torso of the child.

14. The method of claim 11, wherein each proximal leg segment of the first and second leg flaps includes a first cutout and a second cutout, wherein the method further comprises selectively inserting each distal leg segment of the first and second leg flaps into one of the first and second cutouts of the corresponding proximal leg segment to selectively vary a size of an opening defined by each of the first and second leg flaps when in the second, closed configuration.

15. The method of claim 11, wherein the distal arm segments of the first and second arm flaps include at least one attachment hole, and wherein the method further comprises attaching an attachment to the attachment holes to secure the pediatric position holder in the second, closed configuration.

16. The method of claim 11, wherein the central panel includes at least one central cutout, and wherein the method further comprises imaging the torso of the child through the at least one central cutout.

17. The method of claim 16, wherein the imaging includes at least one of ultrasound imaging, X-ray imaging, computed tomography, magnetic resonance imaging, and positron emission tomography.

\* \* \* \* \*